US 6,750,183 B2

(12) United States Patent
Gutierrez et al.

(10) Patent No.: US 6,750,183 B2
(45) Date of Patent: Jun. 15, 2004

(54) LUBRICATING OIL COMPOSITION (75) Inventors: Antonio Gutierrez, Mercerville, NJ (US); Ricardo A. Bloch, Scotch Plains, NJ (US); Nancy Z. Diggs, Westfield, NJ (US); Fredrick W. Girschick, Scotch Plains, NJ (US); David J. Martella, Princeton, NJ (US); Mark G. Stevens, Metuchen, NJ (US); Jacob Emert, Brooklyn, NY (US)

(73) Assignee: Infineum International Ltd. (GB)

( * ) Notice: Subject to any disclaimer, the term of this patent is extended or adjusted under 35 U.S.C. 154(b) by 269 days.

(21) Appl. No.: 09/746,044

(22) Filed: Dec. 22, 2000

(65) Prior Publication Data
US 2002/0115575 A1 Aug. 22, 2002

(51) Int. Cl.$^7$ .................. C10M 129/00; C10M 145/00; C10M 133/00; C10M 151/00; C10M 135/00
(52) U.S. Cl. ............... 508/329; 508/332; 508/387; 508/452; 508/457; 508/465; 508/543; 508/552; 508/463; 508/518; 508/565; 508/575; 508/580; 508/578; 508/585; 528/271; 528/310; 528/367; 528/373
(58) Field of Search .................. 508/578, 580, 508/585, 552, 465, 463, 518, 543, 457, 452, 329, 332, 565; 528/271, 310, 367, 373

(56) References Cited

U.S. PATENT DOCUMENTS

| | | | |
|---|---|---|---|
| 1,815,022 A | | 7/1931 | Davis |
| 2,249,564 A | * | 7/1941 | Lieber .................. 508/296 |
| 2,270,062 A | | 1/1942 | Lieber .................. 252/57 |
| 2,315,063 A | * | 3/1943 | Lieber .................. 508/578 |
| 3,520,809 A | * | 7/1970 | Sparks .................. 508/578 |
| 3,676,346 A | * | 7/1972 | Hu .................. 508/295 |
| 4,708,809 A | | 11/1987 | Davis .................. 252/33.4 |
| 4,941,985 A | | 7/1990 | Benfaremo et al. .... 252/51.5 R |
| 5,075,383 A | * | 12/1991 | Migdal et al. .......... 525/293 |
| 5,182,041 A | | 1/1993 | Benfarmeo et al. ..... 252/51.5 A |

FOREIGN PATENT DOCUMENTS

| | | | |
|---|---|---|---|
| WO | WO87/04180 | 7/1987 | ............. C10L/1/16 |
| WO | WO89/00186 | 1/1989 | ........ C10M/127/06 |

OTHER PUBLICATIONS

"Chemical Modifications of Furan–Based Calixarenes by Diels–Alder Reaction", Cafeo, Grazia et al. Chemistry—A European Journal (1999), 5(1), 356–358, vol. 5, No. 1, XP002209075.

* cited by examiner

Primary Examiner—Jacqueline V. Howard (57) ABSTRACT

Lubricating oil compositions providing superior soot dispersing characteristics, which contain a combination of a high molecular weight dispersant and a soot dispersant comprising a linked aromatic oligomer.

15 Claims, 1 Drawing Sheet

LUBRICATING OIL COMPOSITION

FIELD OF THE INVENTION

This invention relates to crankcase lubricating oil compositions. More specifically, the invention is directed to lubricating oil compositions that exhibit soot dispersing characteristics sufficient to allow the lubricating oil composition to pass an industry standard T8 test, with reduced levels of additive nitrogen.

BACKGROUND OF THE INVENTION

Lubricating oil compositions comprise a major amount of a base oil and additives that improve the performance and increase the useful life of the lubricant. Nitrogen-containing dispersants are commonly used lubricant additives. The function of a dispersant is to maintain in suspension within the oil, insoluble materials formed by oxidation and other mechanisms during use of the oil, to prevent sludge flocculation and precipitation of the insoluble materials. Another function of the dispersant is to reduce the agglomeration of soot particles, thus reducing increases in the viscosity of the lubricating oil upon use. Crankcase lubricants providing improved performance, including improved soot dispersancy, have been continuously demanded.

To improve soot dispersancy, the industry has moved to the use higher molecular weight materials, which have superior dispersancy properties compared to lower molecular weight materials, and to use the high molecular weight dispersants in ever increasing amounts. However, dispersants are expensive. Further, common methods for forming high molecular weight, nitrogen-containing dispersants leave residual chlorine, which is introduced into the lubricant with the dispersant. The presence of chlorine leads to problems with the disposal of used lubricants, and lubricants containing reduced amounts of chlorine have been demanded. Also, greater levels of high molecular weight dispersant do not blend well in lubricants also containing overbased detergents. Still further, a high level of basic amine from dispersants contributes to the deterioration of seals within the engine during service. Therefore, it would be advantageous to provide a lubricant with adequate soot dispersancy properties using reduced amounts of high molecular weight, nitrogen-containing dispersant.

U.S. Pat. No. 1,815,022 to Davis (1931) discloses condensates of naphthalene and essentially linear chlorinated waxes formed by Freidel Craft alkylation of the naphthalene. Such compounds were described as functioning as wax crystal modifiers or lube oil flow improver (LOFI) additives and were added to oil to improve the cold flow characteristics thereof. These compounds have not been used for a number of years and, due to a high chlorine content, these compounds would be considered unsuitable for use in a modern passenger car, or heavy duty diesel motor oil formulations. In modern formulations, these compounds have been supplanted by fumarate/vinyl acetate copolymers or polymethacrylate-based LOFIs.

U.S. Pat. No. 4,708,809 to Davis describes a lubricating oil composition containing a phenolic compound of the formula:

$$(R)_a—Ar—(OH)_b$$

wherein R is a saturated hydrocarbon group having 10 or more aliphatic carbon atoms; a and b are each independently 1 to 3 times the number of aromatic nuclei present in Ar; and Ar is a single, fused or linked polynuclear ring moiety that is optionally substituted. It is alleged that the addition of a minor amount of such a compound to a lubricant composition that is mixed with fuel will lead to a reduction in piston ring sticking in a two cycle engine.

SUMMARY OF THE INVENTION

The present invention, in brief summary, is directed to crankcase lubricating oils comprising a major amount by weight of an oil of lubricating viscosity; a minor amount by weight of a high molecular weight, nitrogen-containing dispersant; and an amount of an oil soluble, or oil dispersible aromatic hydrocarbyl oligomer sufficient to provide the lubricating composition with improved soot dispersing properties.

DETAILED DESCRIPTION OF THE INVENTION

The lubricating oil compositions of the present invention comprise a major amount of an oil of lubricating viscosity. Oils of lubricating viscosity useful in the context of the present invention may be selected from natural lubricating oils, synthetic lubricating oils and mixtures thereof. The lubricating oil may range in viscosity from light distillate mineral oils to heavy lubricating oils such as gasoline engine oils, mineral lubricating oils and heavy duty diesel oils. Generally, the viscosity of the oil ranges from about 2 centistokes to about 40 centistokes, especially from about 4 centistokes to about 20 centistokes, as measured at 100°0 C.

Natural oils include animal oils and vegetable oils (e.g., castor oil, lard oil); liquid petroleum oils and hydrorefined, solvent-treated or acid-treated mineral oils of the paraffinic, naphthenic and mixed paraffinic-naphthenic types. Oils of lubricating viscosity derived from coal or shale also serve as useful base oils.

Synthetic lubricating oils include hydrocarbon oils and halo-substituted hydrocarbon oils such as polymerized and interpolymerized olefins (e.g., polybutylenes, polypropylenes, propylene-isobutylene copolymers, chlorinated polybutylenes, poly(1-hexenes), poly(1-octenes), poly(1-decenes)); alkylbenzenes (e.g., dodecylbenzenes, tetradecylbenzenes, dinonylbenzenes, di(2-ethylhexyl) benzenes); polyphenyls (e.g., biphenyls, terphenyls, alkylated polyphenols); and alkylated diphenyl ethers and alkylated diphenyl sulfides and derivative, analogs and homologs thereof.

Alkylene oxide polymers and interpolymers and derivatives thereof where the terminal hydroxyl groups have been modified by esterification, etherification, etc., constitute another class of known synthetic lubricating oils. These are exemplified by polyoxyalkylene polymers prepared by polymerization of ethylene oxide or propylene oxide, and the alkyl and aryl ethers of polyoxyalkylene polymers (e.g., methyl-polyiso-propylene glycol ether having a molecular weight of 1000 or diphenyl ether of poly-ethylene glycol having a molecular weight of 1000 to 1500); and mono- and polycarboxylic esters thereof, for example, the acetic acid esters, mixed $C_3$–$C_8$ fatty acid esters and $C_{13}$ oxo acid diester of tetraethylene glycol.

Another suitable class of synthetic lubricating oils comprises the esters of dicarboxylic acids (e.g., phthalic acid, succinic acid, alkyl succinic acids and alkenyl succinic acids, maleic acid, azelaic acid, suberic acid, sebasic acid, fumaric acid, adipic acid, linoleic acid dimer, malonic acid, alkylmalonic acids, alkenyl malonic acids) with a variety of alcohols (e.g., butyl alcohol, hexyl alcohol, dodecyl alcohol, 2-ethylhexyl alcohol, ethylene glycol, diethylene glycol monoether, propylene glycol). Specific examples of such esters includes dibutyl adipate, di(2-ethylhexyl) sebacate, di-n-hexyl fumarate, dioctyl sebacate, diisooctyl azelate, diisodecyl azelate, dioctyl phthalate, didecyl phthalate, dieicosyl sebacate, the 2-ethylhexyl diester of linoleic acid dimer, and the complex ester formed by reacting one mole of sebacic acid with two moles of tetraethylene glycol and two moles of 2-ethylhexanoic acid.

Esters useful as synthetic oils also include those made from $C_5$ to $C_{12}$ monocarboxylic acids and polyols and polyol esters such as neopentyl glycol, trimethylolpropane, pentaerythritol, dipentaerythritol and tripentaerythritol.

Silicon-based oils such as the polyalkyl-, polyaryl-, polyalkoxy- or polyaryloxysilicone oils and silicate oils comprise another useful class of synthetic lubricants; such oils include tetraethyl silicate, tetraisopropyl silicate, tetra-(2-ethylhexyl)silicate, tetra-(4-methyl-2-ethylhexyl)silicate, tetra-(p-tert-butyl-phenyl) silicate, hexa-(4-methyl-2-ethylhexyl)disiloxane, poly(methyl)siloxanes and poly (methylphenyl)siloxanes. Other synthetic lubricating oils include liquid esters of phosphorous-containing acids (e.g., tricresyl phosphate, trioctyl phosphate, diethyl ester of decylphosphonic acid) and polymeric tetrahydrofurans.

Unrefined, refined and re-refined oils can be used in lubricants of the present invention. Unrefined oils are those obtained directly from a natural or synthetic source without further purification treatment. For example, a shale oil obtained directly from retorting operations; petroleum oil obtained directly from distillation; or ester oil obtained directly from an esterification and used without further treatment would be an unrefined oil. Refined oils are similar to unrefined oils except that the oil is further treated in one or more purification steps to improve one or more properties. Many such purification techniques, such as distillation, solvent extraction, acid or base extraction, filtration and percolation are known to those skilled in the art. Re-refined oils are obtained by processes similar to those used to provide refined oils but begin with oil that has already been used in service. Such re-refined oils are also known as reclaimed or reprocessed oils and are often subjected to additional processing using techniques for removing spent additives and oil breakdown products.

HIGH MOLECULAR WEIGHT DISPERSANT

The high molecular weight dispersants useful in the context of the present invention include the range of higher molecular weight ashless (metal-free) dispersants known to be effective to reduce formation of deposits upon use in gasoline and diesel engines, when added to lubricating oils. The ashless, high molecular weight dispersant useful in the compositions of the present invention comprises an oil soluble polymeric long chain backbone having functional groups capable of associating with particles to be dispersed. Typically, such dispersants comprise amine, alcohol, amide or ester polar moieties attached to the polymer backbone, often via a bridging group. The ashless, high molecular weight dispersant may be, for example, selected from oil soluble salts, esters, amino-esters, amides, imides and oxazolines of long chain hydrocarbon-substituted mono- and polycarboxylic acids or anhydrides thereof; thiocarboxylate derivatives of long chain hydrocarbons; long chain aliphatic hydrocarbons having polyamine moieties attached directly thereto; and Mannich condensation products formed by condensing a long chain substituted phenol with formaldehyde and polyalkylene polyamine.

A "high molecular weight" dispersant is one having a number average molecular weight greater than or equal to 4,000, such as between 4,000 and 20,000. The precise molecular weight ranges will depend on the type of polymer used to form the dispersant, the number of functional groups present, and the type of polar functional group employed. For example, for a polyisobutylene derivatized dispersant, a high molecular weight dispersant is one formed with a polymer backbone having a number average molecular weight of from about 1700 to about 5600. Typical commercially available polyisobutylene-based dispersants contain polyisobutylene polymers having a number average molecular weight ranging from about 900 to about 2300, functionalized by maleic anhydride (MW=98), and derivatized with polyamines having a molecular weight of from about 100 to about 350. Polymers of lower molecular weight may also be used to form high molecular weight dispersants by incorporating multiple polymer chains into the dispersant, which can be accomplished using methods known in the art.

Polymer molecular weight, specifically $\overline{M}n$, can be determined by various known techniques. One convenient method is gel permeation chromatography (GPC), which additionally provides molecular weight distribution information (see W. W. Yau, J. J. Kirkland and D. D. Bly, "Modem Size Exclusion Liquid Chromatography", John Wiley and Sons, New York, 1979). If the molecular weight of an amine-containing dispersant (e.g., PIBSApolyamine or PIBSA-PAM) is being determined, the presence of the amine may cause the dispersant to be adsorbed by the column, leading to an inaccurate molecular weight determination. Persons familiar with the operation of GPC equipment understand that this problem may be eliminated by using a mixed solvent system, such as tetrahydrofuran (THF) mixed with a minor amount of pyridine, as opposed to pure THF. The problem may also be addressed by capping the amine with acetic anhydride and correcting the molecular weight based on the number of capping groups. Another useful method for determining molecular weight, particularly for lower molecular weight polymers, is vapor pressure osmometry (see, e.g., ASTM D3592).

The degree of polymerisation DP of a polymer is:

$$D_p = \sum_i \frac{Mn \times mol. \% \text{ monomer } i}{100 \times mol. \text{ wt monomer } i}$$

and thus for the copolymers of two monomers $D_P$ may be calculated as follows:

$$D_p = \frac{Mn \times mol. \% \text{ monomer } 1}{100 \times mol. \text{ wt monomer } 1} + \frac{Mn \times mol. \% \text{ monomer } 2}{100 \times mol. \text{ wt monomer } 2}$$

Preferably, the degree of polymerisation for the polymer backbones used in the invention is at least 30, typically from 30 to 165, more preferably 35 to 100.

The preferred hydrocarbons or polymers employed in this invention include homopolymers, interpolymers or lower molecular weight hydrocarbons. One family of useful polymers comprise polymers of ethylene and/or at least one $C_3$ to $C_{28}$ alpha-olefin having the formula $H_2C=CHR^1$, wherein $R^1$ is straight or branched chain alkyl radical comprising 1 to 26 carbon atoms and wherein the polymer contains carbon-to-carbon unsaturation, preferably a high degree of terminal ethenylidene unsaturation. One preferred class of such polymers employed in this invention comprise interpolymers of ethylene and at least one alpha-olefin of the above formula, wherein $R^1$ is alkyl of from 1 to 18 carbon atoms, and more preferably is alkyl of from 1 to 8 carbon atoms, and more preferably still of from 1 to 2 carbon atoms. Therefore, useful alpha-olefin monomers and comonomers include, for example, propylene, butene-1, hexene-1, octene-1,4-methylpentene-1, decene-1, dodecene-1, tridecene-1, tetradecene-1, pentadecene-1, hexadecene-1, heptadecene-1, octadecene-1, nonadecene-1, and mixtures thereof (e.g., mixtures of propylene and butene-1, and the like). Exemplary of such polymers are propylene homopolymers, butene-1 homopolymers, propylene-butene copolymers, ethylene-propylene copolymers, ethylene-butene-1 copolymers and the like, wherein the polymer contains at least some terminal and/or internal unsaturation. Preferred polymers are unsaturated copolymers of ethylene and propylene and ethylene and butene-1. The interpolymers of this invention may contain a minor amount, e.g. 0.5 to 5 mole % of a $C_4$ to $C_{18}$ non-conjugated diolefin comonomer. However, it is preferred that the polymers of this invention comprise only alpha-olefin homopolymers, interpolymers of alpha-olefin comonomers and interpolymers of ethylene and alpha-olefin comonomers. The molar ethylene content of the polymers employed in this invention is preferably in the range of 20 to 80%, and more preferably 30 to 70%. When propylene and/or butene-1 are employed as comonomer(s) with ethylene, the ethylene content of such copolymers is most preferably between 45 and 65%, although higher or lower ethylene contents may be present.

These polymers may be prepared by polymerizing alpha-olefin monomer, or mixtures of alpha-olefin monomers, or mixtures comprising ethylene and at least one $C_3$ to $C_{28}$ alpha-olefin monomer, in the presence of a catalyst system comprising at least one metallocene (e.g., a cyclopentadienyl-transition metal compound) and an aluminoxane compound. Using this process, a polymer in which 95% or more of the polymer chains possess terminal ethenylidene-type unsaturation can be provided. The percentage of polymer chains exhibiting terminal ethenylidene unsaturation may be determined by FTIR spectroscopic analysis, titration, or $C^{13}$ NMR. Interpolymers of this latter type may be characterized by the formula POLY-C($R^1$)=$CH_2$ wherein $R^1$ is $C_1$ to $C_{26}$ alkyl, preferably $C_1$ to $C_{18}$ alkyl, more preferably $C_1$ to $C_8$ alkyl, and most preferably $C_1$ to $C_2$ alkyl, (e.g., methyl or ethyl) and wherein POLY represents the polymer chain. The chain length of the $R^1$ alkyl group will vary depending on the comonomer(s) selected for use in the polymerization. A minor amount of the polymer chains can contain terminal ethenyl, i.e., vinyl, unsaturation, i.e. POLY-CH=$CH_2$, and a portion of the polymers can contain internal monounsaturation, e.g. POLY-CH=CH($R^1$), wherein $R^1$ is as defined above. These terminally unsaturated interpolymers may be prepared by known metallocene chemistry and may also be prepared as described in U.S. Pat. Nos. 5,498,809; 5,663,130; 5,705,577; 5,814,715; 6,022,929 and 6,030,930.

Another useful class of polymers is polymers prepared by cationic polymerization of isobutene, styrene, and the like. Common polymers from this class include polyisobutenes obtained by polymerization of a $C_4$ refinery stream having a butene content of about 35 to about 75% by wt., and an isobutene content of about 30 to about 60% by wt., in the presence of a Lewis acid catalyst, such as aluminum trichloride or boron trifluoride. A preferred source of monomer for making poly-n-butenes is petroleum feedstreams such as Raffinate II. These feedstocks are disclosed in the art such as in U.S. Pat. No. 4,952,739. Polyisobutylene is a most preferred backbone of the present invention because it is readily available by cationic polymerization from butene streams (e.g., using $AlCl_3$ or $BF_3$ catalysts). Such polyisobutylenes generally contain residual unsaturation in amounts of about one ethylenic double bond per polymer chain, positioned along the chain.

As noted above, the polyisobutylene polymers employed are generally based on a hydrocarbon chain of from about 900 to 2,300. Methods for making polyisobutylene are known. Polyisobutylene can be functionalized by halogenation (e.g. chlorination), the thermal "ene" reaction, or by free radical grafting using a catalyst (e.g. peroxide), as described below.

Processes for reacting polymeric hydrocarbons with unsaturated carboxylic acids, anhydrides or esters and the preparation of derivatives from such compounds are disclosed in U.S. Pat. Nos. 3,087,936; 3,172,892; 3,215,707; 3,231,587; 3,272,746; 3,275,554; 3,381,022; 3,442,808; 3,565,804; 3,912,764; 4,110,349; 4,234,435; and GB-A-1,440,219. The polymer or hydrocarbon may be functionalized, for example, with carboxylic acid producing moieties (preferably acid or anhydride) by reacting the polymer or hydrocarbon under conditions that result in the addition of functional moieties or agents, i.e., acid, anhydride, ester moieties, etc., onto the polymer or hydrocarbon chains primarily at sites of carbon-to-carbon unsaturation (also referred to as ethylenic or olefinic unsaturation) using the halogen assisted functionalization (e.g. chlorination) process or the thermal "ene" reaction.

When using the free radical grafting process employing a catalyst (e.g. peroxide), the functionalization is randomly effected along the polymer chain. Selective functionalization can be accomplished by halogenating, e.g., chlorinating or brominating the unsaturated (α-olefin polymer to about 1 to 8 wt. %, preferably 3 to 7 wt. % chlorine, or bromine, based on the weight of polymer or hydrocarbon, by passing the chlorine or bromine through the polymer at a temperature of 60 to 250° C., preferably 110 to 160° C., e.g., 120 to 140° C., for about 0.5 to 10, preferably 1 to 7 hours. The halogenated polymer or hydrocarbon (hereinafter backbones) can then be reacted with sufficient monounsaturated reactant capable of adding functional moieties to the backbone, e.g., monounsaturated carboxylic reactant, at 100 to 250° C., usually about 180° C. to 235° C., for about 0.5 to 10, e.g., 3 to 8 hours, such that the product obtained will contain the desired number of moles of the monounsaturated carboxylic reactant per mole of the halogenated backbones. Alternatively, the backbone and the monounsaturated carboxylic reactant can be mixed and heated while adding chlorine to the hot material.

The hydrocarbon or polymer backbone can be functionalized, e.g., with carboxylic acid producing moieties (preferably acid or anhydride moieties) selectively at sites of carbon-to-carbon unsaturation on the polymer or hydrocarbon chains, or randomly along chains using the three processes mentioned above, or combinations thereof, in any sequence.

The preferred monounsaturated reactants that are used to functionalize the backbone comprise mono- and dicarboxylic acid material, i.e., acid, anhydride, or acid ester material, including (i) monounsaturated $C_4$ to $C_{10}$ dicarboxylic acid wherein (a) the carboxyl groups are vicinyl, (i.e., located on adjacent carbon atoms) and (b) at least one, preferably both, of said adjacent carbon atoms are part of said mono unsaturation; (ii) derivatives of (i) such as anhydrides or $C_1$ to $C_5$ alcohol derived mono- or diesters of (i); (iii) monounsaturated $C_3$ to $C_{10}$ monocarboxylic acid wherein the carbon—carbon double bond is conjugated with the carboxy group, i.e., of the structure —C=C—CO—; and (iv) derivatives of (iii) such as $C_1$ to $C_5$ alcohol derived mono- or diesters of (iii). Mixtures of monounsaturated carboxylic materials (i)–(iv) also may be used. Upon reaction with the backbone, the monounsaturation of the monounsaturated carboxylic reactant becomes saturated. Thus, for example, maleic anhydride becomes backbone-substituted succinic anhydride, and acrylic acid becomes backbone-substituted propionic acid. Exemplary of such monounsaturated carboxylic reactants are fumaric acid, itaconic acid, maleic acid, maleic anhydride, chloromaleic acid, chloromaleic anhydride, acrylic acid, methacrylic acid, crotonic acid, cinnamic acid, and lower alkyl (e.g., $C_1$ to $C_4$ alkyl) acid esters of the foregoing, e.g., methyl maleate, ethyl fumarate, and methyl fumarate. The monounsaturated carboxylic reactant, preferably maleic anhydride, typically will be used in an amount ranging from about 0.01 to about 20 wt. %, preferably 0.5 to 10 wt. %, based on the weight of the polymer or hydrocarbon.

While chlorination normally helps increase the reactivity of starting olefin polymers with monounsaturated functionalizing reactant, it is not necessary with the polymers or hydrocarbons contemplated for use in the present invention, particularly those preferred polymers or hydrocarbons which possess a high terminal bond content and reactivity. Preferably, therefore, the backbone and the monounsaturated functionality reactant, e.g., carboxylic reactant, are contacted at elevated temperature to cause an initial thermal "ene" reaction to take place. Ene reactions are known.

The hydrocarbon or polymer backbone can be functionalized by random attachment of functional moieties along the polymer chains by a variety of methods. For example, the polymer, in solution or in solid form, may be grafted with the monounsaturated carboxylic reactant, as described above, in the presence of a free-radical initiator. When performed in solution, the grafting takes place at an elevated temperature in the range of about 100 to 260° C., preferably 120 to 240° C. Preferably, free-radical initiated grafting is accomplished in a mineral lubricating oil solution containing, for example, 1 to 50 wt. %, preferably 5 to 30 wt. % polymer based on the initial total oil solution.

The free-radical initiators that may be used are peroxides, hydroperoxides, and azo compounds, preferably those that have a boiling point greater than about 100° C. and decompose thermally within the grafting temperature range to provide free-radicals. Representative of these free-radical initiators are azobutyronitrile, 2,5-dimethylhex-3-ene-2,5-bis-tertiary-butyl peroxide and dicumene peroxide. The initiator, when used, typically is used in an amount of between 0.005% and 1% by weight based on the weight of the reaction mixture solution. Typically, the aforesaid monounsaturated carboxylic reactant material and free-radical initiator are used in a weight ratio range of from about 1.0:1 to 30:1, preferably 3:1 to 6:1. The grafting is preferably carried out in an inert atmosphere, such as under nitrogen blanketing. The resulting grafted polymer is characterized by having carboxylic acid (or ester or anhydride) moieties randomly attached along the polymer chains: it being understood, of course, that some of the polymer chains remain ungrafted. The free radical grafting described above can be used for the other polymers and hydrocarbons of the present invention.

The functionalized oil-soluble polymeric hydrocarbon backbone may then be further derivatized with a nucleophilic reactant, such as an amine, amino-alcohol, alcohol, metal compound, or mixture thereof, to form a corresponding derivative. Useful amine compounds for derivatizing functionalized polymers comprise at least one amine and can comprise one or more additional amine or other reactive or polar groups. These amines may be hydrocarbyl amines or may be predominantly hydrocarbyl amines in which the hydrocarbyl group includes other groups, e.g., hydroxy groups, alkoxy groups, amide groups, nitriles, imidazoline groups, and the like. Particularly useful amine compounds include mono- and polyamines, e.g., polyalkene and polyoxyalkylene polyamines of about 2 to 60, such as 2 to 40 (e.g., 3 to 20) total carbon atoms having about 1 to 12, such as 3 to 12, and preferably 3 to 9 nitrogen atoms per molecule. Mixtures of amine compounds may advantageously be used, such as those prepared by reaction of alkylene dihalide with ammonia. Preferred amines are aliphatic saturated amines, including, for example, 1,2-diaminoethane; 1,3-diaminopropane; 1,4-diaminobutane; 1,6-diaminohexane; polyethylene amines such as diethylene triamine; triethylene tetramine; tetraethylene pentamine; and polypropyleneamines such as 1,2-propylene diamine; and di-(1,2-propylene) triamine.

Other useful amine compounds include: alicyclic diamines such as 1,4-di(aminomethyl) cyclohexane and heterocyclic nitrogen compounds such as imidazolines. Another useful class of amines is the polyamido and related amido-amines as disclosed in U.S. Pat. Nos. 4,857,217; 4,956,107; 4,963,275; and 5,229,022. Also usable is tris (hydroxymethyl)amino methane (TAM) as described in U.S. Pat. Nos. 4,102,798; 4,113,639; 4,116,876; and UK 989,409. Dendrimers, star-like amines, and comb-structured amines may also be used. Similarly, one may use condensed amines, as described in U.S. Pat. No. 5,053,152. The functionalized polymer is reacted with the amine compound using conventional techniques as described, for example, in U.S. Pat. Nos. 4,234,435 and 5,229,022, as well as in EP-A-208,560.

The functionalized, oil-soluble polymeric hydrocarbon backbones may also be derivatized with hydroxy compounds such as monohydric and polyhydric alcohols, or with aromatic compounds such as phenols and naphthols. Preferred polyhydric alcohols include alkylene glycols in which the alkylene radical contains from 2 to 8 carbon atoms. Other useful polyhydric alcohols include glycerol, mono-oleate of glycerol, monostearate of glycerol, monomethyl ether of glycerol, pentaerythritol, dipentaerythritol, and mixtures thereof. An ester dispersant may also be derived from unsaturated alcohols, such as allyl alcohol, cinnamyl alcohol, propargyl alcohol, 1-cyclohexane-3-ol, and oleyl alcohol. Still other classes of alcohols capable of yielding ashless dispersants comprise ether-alcohols, including oxy-alkylene and oxy-arylene. Such ether-alcohols are exemplified by ether-alcohols having up to 150 oxy-alkylene radicals in which the alkylene radical contains from 1 to 8 carbon atoms. The ester dispersants may be di-esters of succinic acids or acid-esters, i.e., partially esterified succinic acids, as well as partially esterified polyhydric alcohols or phenols, i.e., esters having free alcohols or phenolic hydroxy radicals. An ester dispersant may be prepared by any one of several known methods as described, for example, in U.S. Pat. No. 3,381,022.

Preferred groups of dispersant include polyamine-derivatized poly α-olefin, dispersants, particularly ethylene/butene alpha-olefin and polyisobutylene-based dispersants. Particularly preferred are ashless dispersants derived from polyisobutylene substituted with succininc anhydride groups and reacted with polyethylene amines, e.g., polyethylene diamine, tetraethylene pentamine; or a polyoxyalkylene polyamine, e.g., polyoxypropylene diamine, trimethylolaminomethane; a hydroxy compound, e.g., pentaerythritol; and combinations thereof. One particularly preferred dispersant combination is a combination of (A) polyisobutylene substituted with succinic anhydride groups and reacted with (B) a hydroxy compound, e.g., pentaerythritol; (C) a polyoxyalkylene polyamine, e.g., polyoxypropylene diamine, or (D) a polyalkylene diamine, e.g., polyethylene diamine and tetraethylene pentamine using about 0.3 to about 2 moles of (B), (C) and/or (D) per mole of (A). Another preferred dispersant combination comprises a combination of (A) polyisobutenyl succinic anhydride with (B) a polyaLkylene polyamine, e.g., tetraethylene pentamine, and (C) a polyhydric alcohol or polyhydroxy-substituted aliphatic primary amine, e.g., pentaerythritol or trismethylolaminomethane, as described in U.S. Pat. No. 3,632,511.

Another class of ashless dispersants comprises Mannich base condensation products. Generally, these products are prepared by condensing about one mole of an alkyl-substituted mono- or polyhydroxy benzene with about 1 to 2.5 moles of carbonyl compound(s) (e.g., formaldehyde and paraformaldehyde) and about 0.5 to 2 moles of polyalkylene polyamine, as disclosed, for example, in U.S. Pat. No. 3,442,808. Such Mannich base condensation products may include a polymer product of a metallocene catalyzed polymerization as a substituent on the benzene group, or may be reacted with a compound containing such a polymer substituted on a succinic anhydride in a manner similar to that described in U.S. Pat. No. 3,442,808. Examples of functionalized and/or derivatized olefin polymers synthesized using metallocene catalyst systems are described in the publications identified supra.

The dispersant can be further post treated by a variety of conventional post treatments such as boration, as generally taught in U.S. Pat. Nos. 3,087,936 and 3,254,025. Boration of the dispersant is readily accomplished by treating an acyl nitrogen-containing dispersant with a boron compound such as boron oxide, boron halide boron acids, and esters of boron acids, in an amount sufficient to provide from about 0.1 to about 20 atomic proportions of boron for each mole of acylated nitrogen composition. Useful dispersants contain from about 0.05 to about 2.0 wt. %, e.g., from about 0.05 to about 0.7 wt. % boron. The boron, which appears in the product as dehydrated boric acid polymers (primarily $(HBO_2)_3$), is believed to attach to the dispersant imides and diimides as amine salts, e.g., the metaborate salt of the diimide. Boration can be carried out by adding from about 0.5 to 4 wt. %, e.g., from about 1 to about 3 wt. % (based on the weight of acyl nitrogen compound) of a boron compound, preferably boric acid, usually as a slurry, to the acyl nitrogen compound and heating with stirring at from about 135° C. to about 190° C., e.g., 140° C. to 170° C., for from about 1 to about 5 hours, followed by nitrogen stripping. Alternatively, the boron treatment can be conducted by adding boric acid to a hot reaction mixture of the dicarboxylic acid material and amine, while removing water. Other post reaction processes commonly known in the art can also be applied.

The third essential component of the composition of the present invention is substituted aromatic hydrocarbyl oligomer is of the following formula:

(I)

In Formula I, each moiety Ar represents an optionally substituted aromatic moiety; each L is a linking moiety that is carbon—carbon single bond or a linking group, n is a number from about 2 to about 1000, and each T is a terminal group. At least 25% of the aromatic moieties (Ar) are connected to at least 2 linking moieties (L). The ratio of the total number of aliphatic carbon atoms to aromatic ring atoms in the substituted aromatic hydrocarbyl oligomer is from about 0.10:1 to about 40:1.

Aromatic moieties Ar of Formula I can be polynuclear carbocyclic moieties or mono- or polynuclear heterocyclic moieties. Polynuclear carbocyclic moieties may comprise two or more fused rings, each ring having 4 to 10 carbon atoms (e.g., naphthalene). Suitable carbocyclic polynuclear moieties may also be linked mononuclear aromatic moieties, such as biphenyl, or may comprise linked, fused rings (e.g., binaphthyl). Examples of suitable polynuclear carbocyclic aromatic moieties include naphthalene, anthracene, phenanthrene, cyclopentenophenanthrene, benzanthracene, dibenzanthracene, chrysene, pyrene, benzpyrene and coronene and dimer, trimer and higher polymers thereof. Heterocyclic moieties Ar include those comprising one or more rings each containing 4 to 10 atoms, including one or more hetero atoms selected from N, O and S. Examples of suitable monocyclic heterocyclic aromatic moieties include pyrrole, furan, thiophene, imidazole, oxazole, thiazole, pyrazole, pyridine, pyrimidine and purine. Suitable polynuclear heterocyclic moieties Ar include, for example, quinoline, isoquinoline, carbazole, dipyridyl, cinnoline, phthalazine, quinazoline, quinoxaline and phenanthroline. Each aromatic moiety (Ar) may be independently selected such that all moieties (Ar) are the same or different. The preferred polycyclic carbocyclic aromatic moiety is naphthalene. Polycyclic heterocycles are preferred over monocyclic heterocycles. The preferred heterocyclic aromatic moiety is quinoline.

Each aromatic moiety Ar may independently be unsubstituted or substituted with 1 to 6 groups selected from H, —OR$_1$, —N(R$_1$)$_2$, F, Cl, Br, I, -(L-(Ar)-T), —S(O)$_w$R$_1$, —(CZ)$_x$—(Z)$_y$—R, and —(Z)$_y$—(CZ)$_x$—R$_1$, wherein w is 0 to 3, each Z is independently O, —N(R$_1$)$_2$ or S, x and y are independently 0 or 1, each R$_1$ is independently H or a linear or branched, saturated or unsaturated hydrocarbyl group having from 1 to about 200 carbon atoms, optionally mono- or poly-substituted with one or more groups selected from —$OR_2$, —$N(R_2)_2$, F, Cl, Br, I, —$S(O)_wR_2$, —$(CZ)_x$—$(Z)_y$—$R_2$ and —$(Z)_y$—$(CZ)_x$—$R_2$, wherein w, x, y and Z are as defined above, $R_2$ is a hydrocarbyl group having 1 to about 200 carbon atoms, and T is a terminal group. Preferably, at least 60% of the aromatic moieties (Ar) are substituted with at least one of the aforementioned substituent groups other than H. The oligomer must be substituted to provide a ratio of the total number of aliphatic carbons to the total number of aromatic ring atoms that is from about 0.10:1 to about 40:1, preferably from about 0.10:1 to about 15:1, most preferably from about 4:1 to about 7:1.

Each linking group (L) may be the same or different, and can be a carbon to carbon single bond between the carbon atoms of adjacent moieties Ar, or a linking group. Suitable linking groups include alkylene linkages, such as —$R_3$—, ether linkages, such as —O—, —$O(R_3)$—, —O—$((R_3)$—$O)_a$— and —$((R_3)$—$O)_a$—$(R_3)$—; acyl linkages, including —$(CO)_2$—, —$(CO)$—$(R_3)$—, —$(CO)$—$((R_3)$—$(CO))_a$, —$(CO)$—$((R_3)$—$(CO))_a$—$(R_3)$— and —$((R_3)$—$(CO))_a$—$(R_3)$—; ester linkages, such as —$(CO_2)$—, —$(CO_2O$—$R_3O$—, —$(CO_2)$—$((R_3)$—$(CO_2))_a$—, —$(CO_2)$—$((R_3)$—$(CO))_a$—$(R_3)$—, —$((R_3)$—$(CO_2)_a$—$(R_3)$—, —(OCO)—$(R_3)$—, —(OCO)—$((R_3)$—$(OCO))_a$—, and —(OCO)—$((R_3)$—$(CO_3))_a$—; anhydride linkages, including —$(CO_2CO)$—, —$(R_3)$—$(CO_2CO)$— and —$(R_3)$—$(CO_2CO)$—$(R_3)$—; ether-acyl linkages, such as —O—$(R_3)$—(CO)—, —$(R_3)$—O—$(R_3)$—(CO)—, —O—$(R_3)$—(CO)—$(R_3)$—and —$(R_3)$—O—$(R_3)$—(CO)—$(R_3)$—; ether-ester linkages such as —O—$(R_3)$—$(CO_2)$—, —$(R_3)$—O—$(R_3)$—$(CO_2)$—, —O—$(R_3)$—$(CO_2)$—$(R_3)$—, —$(R_3)$—O—$(R_3)$—$(CO_2)$—$(R_3)$—, —O—$(R_3)$—(OCO)—, —$(R_3)$—O—$(R_3)$—(OCO)—, —O—$(R_3)$—(OCO)—$(R_3)$—, and —$(R_3)$—O—$(R_3)$—(OCO)—$(R_3)$—; acyl-ester linkages, including —(CO)—$(R_3)$—$(CO_2)$—, —$(R_3)$—(CO)—$(R_3)$—$(CO_2)$—, —(CO)—$(R_3)$—$(CO_2)$—$(R_3)$—, —$(R_3)$—(CO)—$(R_3)$—$(CO_2)$—$(R_3)$—, —(CO)—$(R_3)$—(OCO)—, —$(R_3)$—(CO)—$(R_3)$—(OCO)—, —(CO)—$(R_3)$—(OCO)—$(R_3)$—, and —$(R_3)$—(CO)—$(R_3)$—(OCO)—$(R_3)$—; amino linkages, such as —$N(R_1)$—, —$N(R_1)$—$(R_3)$—, —$N(R_1)$—$((R_3)$—$N(R_1))_a$—, and —$((R_3)$—$N(R_1)_a$—$(R_3)$—; amido linkages, for example, —$N(R_1)$—(CO)—, —$N(R_1)$—(CO)—$(R_3)$—(CO)—$N(R_1)$—, —(CO)—$N(R_1)$—$(R_3)$—$N(R_1)$—(CO)—, —(CO)—$N(R_1)$—$(R_3)$—(CO)—$N(R_1)$—, —$(R_3)$—$N(R_1)$—(CO)—$(R_3)$—(CO)—$N(R_1)$—$(R_3)$—, —$(R_3)$—(CO)—$N(R_1)$—$(R_3)$—$N(R_1)$—(CO)—$(R_3)$—and —$(R_3)$—(CO)—$N(R_1)$—$(R_3)$—(CO)—$N(R_1)$—$(R_3)$—; carbamido linkages, such as —$N(R_1)$—(CO)—$N(R_1)$—, —$(R_3)$—$N(R_1)$—(CO)—$N(R_1)$—, —$(R_3)$—$N(R_1)$—(CO)—$N(R_1)$—$(R_3)$—; urethane linkages, including —$N(R_1)$—$(CO_2)$—, —$(R_3)$—$N(R_1)$—$(CO_2)$—, —$N(R_1)$—$(CO_2)$—$(R_3)$—, and —$(R_3)$—$N(R_1)$—$(CO_2)$—$(R_3)$—; and sulfur linkages, for example —$S_c$—, —$(R_3)$—$S_c$—, —$(R_3)$—$S_c$—$(R_3)$—, —$SO_d$—, —$(R_3)$—$SO_d$—, —$SO_d$—$[(R_3)$—$SO_d]_a$—, —$SO_d$—$[(R_3)$—$SO_d]_a$—$(R_3)$—and —$[(R_3)$—$SO_d]_a$—$(R_2)$—; wherein $R_1$ is as previously defined, each $R_3$ is independently a linear or branched, saturated or unsaturated hydrocarbyl group having from 1 to about 100 carbon atoms, more preferably from 1 to about 30 carbon atoms, and most preferably from 1 to about 10 carbon atoms, optionally mono- or polysubstituted with $OR_1$, $N(R_1)_2$, F, Cl, Br, I, $S(O)_w$ $R_1$, $(CZ)_x$—$(Z)_y$—$R_1$, $(Z)_y$—$(CZ)_x$—$R_1$, wherein w and Z are as previously defined; a is from about 1 to about 40, b is either 1 or 2, c is from about 1 to about 8, and d is from about 1 to about 3.

Preferred linking groups are alkylene linkages such as —$CH_3CHC(CH_3)_2$—, or —$C(CH_3)_2$—; diacyl linkages such as —COCO— or —$CO(CH_2)_4CO$—; and sulfur linkages, such as —$S_1$— or —$S_2$—. When the aromatic moiety (Ar) is substituted with an OH substituent, the preferred linking group is —$CH_2$—. The number of aliphatic atoms and aromatic carbon atoms in linking moiety (L) are not included when calculating the ratio of aliphatic to of aromatic carbons for the oligomer.

Each terminal group (T) is independently selected from H, $OR_1$, $N(R_1)2$, F, Cl, Br, I, $S(O)_wR_1$, $(CZ)_x$—$(Z)_y$—$R_1$ or $(Z)_y$—$(CZ)_x$—$R_1$, wherein $R_1$, w, x, y and Z are as previously defined.

Methods for forming compounds of Formula I should be apparent to those of ordinary skill in the art. The, aromatic moiety Ar may be substituted by, for example, alkylated, prior to or subsequent to linkage. To form the oligomer of Formula I, individual aromatic moieties Ar may be reacted with a polyhalogenated (preferably dihalogenated) hydrocarbon (e.g., 1,4-dichlorobutane, 2,2-dichloropropane, etc.), or a di- or poly-olefin (e.g., butadiene, isoprene, 1,4-hexadiene, 1,5-hexadiene, etc.) to yield a compound of Formula I having an alkylene linking groups. Reaction of aromatic moieties Ar and a ketone or aldehyde (e.g., formaldehyde, acetone, benzophenone, acetophenone, etc.) provides an alkylene linked compound. An acyl-linked compound can be formed by reacting aromatic moieties Ar with a diacid or anhydride (e.g., oxalic acid, malonic acid, succinic acid, glutaric acid, adipic acid, succinic anhydride, etc.). Sulfide, polysulfide, sulfinyl and sulfonyl linkages may be provided by reacting the aromatic moieties Ar with a suitable difunctional sulfurizing agent (e.g., sulfur monochloride, sulfur dichloride, thionyl chloride ($SOCl_2$), sulfuryl chloride ($SO_2Cl_2$), etc.). To provide a compound of Formula I with an alkylene ether linkage, hydroxy-substituted aromatic moieties Ar can be reacted with a dihalide (e.g., 1,2-dichloroethane, 1,3-diiodopropane, 1,6-dichlorohexane, etc.). Oligomers of Formula I, wherein L is a direct carbon to carbon link, may be formed via oxidative coupling polymerization using a mixture of aluminum chloride and cuprous chloride, as described, for example, by P. Kovacic, et al., *J. Polymer Science: Polymer Chem. Ed.*, 21, 457 (1983). Alternatively, such oligomers may be formed by reacting aromatic moieties Ar and an alkali metal as described, for example, in "Catalytic Benzene Coupling on Caesium/Nanoporous Carbon Catalysts", M. G. Stevens, K. M. Sellers, S. Subramoney and H. C. Foley, *Chemical Communications,* 2679–2680 (1988). The degree of polymerization of the substituted aromatic oligomers of Formula I range from 2 to about 1,000 (corresponding to a value of n of from 1 to about 998), preferably from about 5 to about 200, most preferably from about 10 to about 50.

Novel compounds of Formula I include those wherein each Ar independently represents an aromatic moiety optionally substituted by 1 to 4 substituents selected from H, —$OR_4$, —$N(R_4)_2$, F, Cl, Br, I, -(L-(Ar)-T), —$S(O)_w$ $R_4$, -$(CZ)_x$-$(Z)_y$—$R_4$ and -$(Z)_y$-$(CZ)_x R_4$, wherein w is 0 to 3, each Z is independently O, —$N(R_4)_2$ or S, x and y are independently 0 or 1 and each $R_4$ is independently H, methyl, ethyl, propyl or a branched hydrocarbyl group having 3 to 200 carbon atoms, optionally mono- or poly-substituted with one or more groups selected from —$OR_4$, —$N(R_4)_2$, F, Cl, Br, I, —$S(O)_wR_4$, -$(CZ)_x$-$(Z)_yR_4$ and -$(Z)_y$-$(CZ)_x$—$R_4$, wherein w, x, y, T, $R_4$ and Z are as defined above.

For adequate control of soot induced viscosity increase, a high molecular weight dispersant is conventionally added in an amount of 5 to 12 mass %, based on the total mass of the finished lubricant. These dispersants typically have a nitrogen content of about 1 wt. %. Thus, a typical lubricant composition will contain from about 0.10 wt % to about 0.12 wt. % of nitrogen from dispersant. In contrast, a finished lubricant containing from about 0.005 to 10 wt. % (preferably about 0.1 to about 5 wt. %, more preferably about 0.5 to about 2 wt. %) of an oligomer of Formula I provides comparable soot dispersant characteristics with only about 2.5 to about 9.5 wt. %, preferably about 2 to 3 wt. % of dispersant, which adds to the lubricant composition only about 0.025 to about 0.095 wt. %, preferably from about 0.02 to about 0.03 wt. % of nitrogen. In general, each 0.5 wt. % increase in the amount of oligomer of Formula I could allow up to a 2.5 wt. % reduction in the amount of needed dispersant. A preferred lubricating oil composition of the invention may contain an amount of high molecular weight dispersant in an amount providing from about 0.008 to about 0.32 wt. % of nitrogen, and an oligomer of Formula I in an amount of from about 0.005 to about 10 wt. %, based on the total weight of lubricating oil composition.

OTHER ADDITIVE COMPONENTS

Additional additives may be incorporated in the compositions of the invention to enable them to meet particular requirements. Examples of additives which may be included in the lubricating oil compositions are detergents, metal rust inhibitors, viscosity index improvers, corrosion inhibitors, oxidation inhibitors, friction modifiers, other dispersants, anti-foaming agents, anti-wear agents and pour point depressants. Some are discussed in further detail below.

Metal-containing or ash-forming detergents function both as detergents to reduce or remove deposits and as acid neutralizers or rust inhibitors, thereby reducing wear and corrosion and extending engine life. Detergents generally comprise a polar head with a long hydrophobic tail, with the polar head comprising a metal salt of an acidic organic compound. The salts may contain a substantially stoichiometric amount of the metal in which case they are usually described as normal or neutral salts, and would typically have a total base number or TBN (as can be measured by ASTM D2896) of from 0 to 80. A large amount of a metal base may be incorporated by reacting excess metal compound (e.g., an oxide or hydroxide) with an acidic gas (e.g., carbon dioxide). The resulting overbased detergent comprises neutralized detergent as the outer layer of a metal base (e.g. carbonate) micelle. Such overbased detergents may have a TBN of 150 or greater, and typically will have a TBN of from 250 to 450 or more.

Detergents that may be used include oil-soluble neutral and overbased sulfonates, phenates, sulfurized phenates, thiophosphonates, salicylates, and naphthenates and other oil-soluble carboxylates of a metal, particularly the alkali or alkaline earth metals, e.g., sodium, potassium, lithium, calcium, and magnesium. The most commonly used metals are calcium and magnesium, which may both be present in detergents used in a lubricant, and mixtures of calcium and/or magnesium with sodium. Particularly convenient metal detergents are neutral and overbased calcium sulfonates having TBN of from 20 to 450 TBN, and neutral and overbased calcium phenates and sulfurized phenates having TBN of from 50 to 450. Combinations of detergents, whether overbased or neutral or both, may be used.

Sulfonates may be prepared from sulfonic acids which are typically obtained by the sulfonation of alkyl substituted aromatic hydrocarbons such as those obtained from the fractionation of petroleum or by the alkylation of aromatic hydrocarbons. Examples included those obtained by alkylating benzene, toluene, xylene, naphthalene, diphenyl or their halogen derivatives such as chlorobenzene, chlorotoluene and chloronaphthalene. The alkylation may be carried out in the presence of a catalyst with alkylating agents having from about 3 to more than 70 carbon atoms. The alkaryl sulfonates usually contain from about 9 to about 80 or more carbon atoms, preferably from about 16 to about 60 carbon atoms per alkyl substituted aromatic moiety.

The oil soluble sulfonates or alkaryl sulfonic acids may be neutralized with oxides, hydroxides, alkoxides, carbonates, carboxylate, sulfides, hydrosulfides, nitrates, borates and ethers of the metal. The amount of metal compound is chosen having regard to the desired TBN of the final product but typically ranges from about 100 to 220 wt. % (preferably at least 125 wt. %) of that stoichiometrically required.

Metal salts of phenols and sulfurized phenols are prepared by reaction with an appropriate metal compound such as an oxide or hydroxide and neutral or overbased products may be obtained by methods well known in the art. Sulfurized phenols may be prepared by reacting a phenol with sulfur or a sulfur containing compound such as hydrogen sulfide, sulfur monohalide or sulfur dihalide, to form products which are generally mixtures of compounds in which 2 or more phenols are bridged by sulfur containing bridges.

Dihydrocarbyl dithiophosphate metal salts are frequently used as antiwear and antioxidant agents. The metal may be an alkali or alkaline earth metal, or aluminum, lead, tin, molybdenum, manganese, nickel or copper. The zinc salts are most commonly used in lubricating oil in amounts of 0.1 to 10, preferably 0.2 to 2 wt. %, based upon the total weight of the lubricating oil composition. They may be prepared in accordance with known techniques by first formiing a dihydrocarbyl dithiophosphoric acid (DDPA), usually by reaction of one or more alcohol or a phenol with $P_2S_5$ and then neutralizing the formed DDPA with a zinc compound. For example, a dithiophosphoric acid may be made by reacting mixtures of primary and secondary alcohols. Alternatively, multiple dithiophosphoric acids can be prepared where the hydrocarbyl groups on one are entirely secondary in character and the hydrocarbyl groups on the others are entirely primary in character. To make the zinc salt, any basic or neutral zinc compound could be used but the oxides, hydroxides and carbonates are most generally employed. Commercial additives frequently contain an excess of zinc due to the use of an excess of the basic zinc compound in the neutralization reaction.

The preferred zinc dihydrocarbyl dithiophosphates are oil soluble salts of dihydrocarbyl dithiophosphoric acids and may be represented by the following formula:

wherein R and R' may be the same or different hydrocarbyl radicals containing from 1 to 18, preferably 2 to 12, carbon atoms and including radicals such as alkyl, alkenyl, aryl, arylalkyl, alkaryl and cycloaliphatic radicals. Particularly preferred as R and $R^1$ groups are alkyl groups of 2 to 8 carbon atoms. Thus, the radicals may, for example, be ethyl, n-propyl, i-propyl, n-butyl, i-butyl, sec-butyl, amyl, n-hexyl, i-hexyl, n-octyl, decyl, dodecyl, octadecyl, 2-ethylhexyl, phenyl, butylphenyl, cyclohexyl, methylcyclopentyl, propenyl, butenyl. In order to obtain oil solubility, the total number of carbon atoms (i.e. R and R') in the dithiophosphoric acid will generally be about 5 or greater. The zinc dihydrocarbyl dithiophosphate can therefore comprise zinc dialkyl dithiophosphates. The present invention may be particularly useful when used with lubricant compositions containing phosphorus levels of from about 0.02 to about 0.12 wt. %, preferably from about 0.03 to about 0.10 wt. %, most preferably from about 0.05 to about 0.08 wt. %, based on the total weight of the composition.

Oxidation inhibitors or antioxidants reduce the tendency of mineral oils to deteriorate in service. Oxidative deterioration can be evidenced by sludge in the lubricant, varnish-like deposits on the metal surfaces, and by viscosity growth. Such oxidation inhibitors include hindered phenols, alkaline earth metal salts of alkylphenolthioesters having preferably $C_5$ to $C_{12}$ alkyl side chains, calcium nonylphenol sulfide, oil soluble phenates and sulfurized phenates, phosphosulfurized or sulfurized hydrocarbons, phosphorous esters, metal thiocarbamates, oil soluble copper compounds as described in U.S. Pat. No. 4,867,890, and molybdenum-containing compounds.

Aromatic amines having at least two aromatic groups attached directly to the nitrogen constitute another class of compounds that is frequently used for antioxidancy. While these materials may be used in small amounts, preferred embodiments of the present invention are free of these compounds. They are preferably used in only small amounts, i.e., up to 0.4 wt. %, or more preferably avoided altogether other than such amount as may result as an impurity from another component of the composition.

Typical oil soluble aromatic amines having at least two aromatic groups attached directly to one amine nitrogen contain from 6 to 16 carbon atoms. The amines may contain more than two aromatic groups. Compounds having a total of at least three aromatic groups in which two aromatic groups are linked by a covalent bond or by an atom or group (e.g., an oxygen or sulfur atom, or a —CO—, —SO$_2$— or alkylene group) and two are directly attached to one amine nitrogen also considered aromatic amines having at least two aromatic groups attached directly to the nitrogen. The aromatic rings are typically substituted by one or more substituents selected from alkyl, cycloalkyl, alkoxy, aryloxy, acyl, acylamino, hydroxy, and nitro groups. The amount of any such oil soluble aromatic amines having at least two aromatic groups attached directly to one amine nitrogen should preferably not exceed 0.4 wt. % active ingredient.

Representative examples of suitable viscosity modifiers are polyisobutylene, copolymers of ethylene and propylene, polymethacrylates, methacrylate copolymers, copolymers of an unsaturated dicarboxylic acid and a vinyl compound, interpolymers of styrene and acrylic esters, and partially hydrogenated copolymers of styrene/isoprene, styrene/butadiene, and isoprene/butadiene, as well as the partially hydrogenated homopolymers of butadiene and isoprene.

Friction modifiers and fuel economy agents that are compatible with the other ingredients of the final oil may also be included. Examples of such materials include glyceryl monoesters of higher fatty acids, for example, glyceryl mono-oleate; esters of long chain polycarboxylic acids with diols, for example, the butane diol ester of a dimerized unsaturated fatty acid; oxazoline compounds; and alkoxylated alkyl-substituted mono-amines, diamines and alkyl ether amines, for example, ethoxylated tallow amine and ethoxylated tallow ether amine.

A viscosity index improver dispersant functions both as a viscosity index improver and as a dispersant. Examples of viscosity index improver dispersants include reaction products of amines, for example polyamines, with a hydrocarbyl-substituted mono -or dicarboxylic acid in which the hydrocarbyl substituent comprises a chain of sufficient length to impart viscosity index improving properties to the compounds. In general, the viscosity index improver dispersant may be, for example, a polymer of a $C_4$ to $C_{24}$ unsaturated ester of vinyl alcohol or a $C_3$ to $C_{10}$ unsaturated mono-carboxylic acid or a $C_4$ to $C_{10}$ di-carboxylic acid with an unsaturated nitrogen-containing monomer having 4 to 20 carbon atoms; a polymer of a $C_2$ to $C_{20}$ olefin with an unsaturated $C_3$ to $C_{10}$ mono- or di-carboxylic acid neutralised with an amine, hydroxyamine or an alcohol; or a polymer of ethylene with a $C_3$ to $C_{20}$ olefin further reacted either by grafting a $C_4$ to $C_{20}$ unsaturated nitrogen-containing monomer thereon or by grafting an unsaturated acid onto the polymer backbone and then reacting carboxylic acid groups of the grafted acid with an amine, hydroxy amine or alcohol.

Pour point depressants, otherwise known as lube oil flow improvers (LOFI), lower the minimum temperature at which the fluid will flow or can be poured. Such additives are well known. Typical of those additives that improve the low temperature fluidity of the fluid are $C_8$ to $C_{18}$ dialkyl fumarate/vinyl acetate copolymers, and polymethacrylates. Foam control can be provided by an antifoamant of the polysiloxane type, for example, silicone oil or polydimethyl siloxane.

Some of the above-mentioned additives can provide a multiplicity of effects; thus for example, a single additive may act as a dispersant-oxidation inhibitor. This approach is well known and need not be further elaborated herein.

In the present invention it may be necessary to include an additive which maintains the stability of the viscosity of the blend. Thus, although polar group-containing additives achieve a suitably low viscosity in the pre-blending stage it has been observed that some compositions increase in viscosity when stored for prolonged periods. Additives which are effective in controlling this viscosity increase include the long chain hydrocarbons functionalized by reaction with mono- or dicarboxylic acids or anhydrides which are used in the preparation of the ashless dispersants as hereinbefore disclosed.

When lubricating compositions contain one or more of the above-mentioned additives, each additive is typically blended into the base oil in an amount that enables the additive to provide its desired function.

It may be desirable, although not essential, to prepare one or more additive concentrates comprising additives (concentrates sometimes being referred to as additive packages) whereby several additives can be added simultaneously to the oil to form the lubricating oil composition.

The final lubricant composition may employ from 5 to 25 mass %, preferably 5 to 18 mass %, typically 10 to 15 mass % of the concentrate, the remainder being oil of lubricating viscosity.

When lubricating compositions contain one or more of the above-mentioned additives, each additive is typically blended into the base oil in an amount that enables the additive to provide its desired function. Representative effect amounts of such additives, when used in crankcase lubricants, are listed below. All the values listed are stated as mass percent active ingredient.

| ADDITIVE | MASS % (Broad) | MASS % (Preferred) |
|---|---|---|
| Metal Detergents | 0.1–15 | 0.2–9 |
| Corrosion Inhibitor | 0–5 | 0–1.5 |
| Metal Dihydrocarbyl Dithiophosphate | 0.1–6 | 0.1–4 |
| Antioxidant | 0–5 | 0.01–2 |
| Pour Point Depressant | 0.01–5 | 0.01–1.5 |
| Antifoaming Agent | 0–5 | 0.001–0.15 |
| Supplemental Antiwear Agents | 0–1.0 | 0–0.5 |
| Friction Modifier | 0–5 | 0–1.5 |
| Viscosity Modifier | 0.01–10 | 0.25–3 |
| Basestock | Balance | Balance |

All weight percents expressed herein (unless otherwise indicated) are based on active ingredient (A.I.) content of the additive, and/or upon the total weight of any additive-package, or formulation which will be the sum of the A.I. weight of each additive plus the weight of total oil or diluent.

This invention will be further understood by reference to the following examples, wherein all parts are parts by weight, unless otherwise noted.

EXAMPLES

Synthesis Example A

Alkylation of Naphthalene

About 0.4 mole (51.2 g) naphthalene, 1.0 mole (252 g) of 1-octadecene, and 200 ml of heptane are charged into a reaction flask. About 2 g of boron trifluoride were bubbled into the liquid and stirred under nitrogen. The reaction flask was then heated to 40° C. to dissolve the naphthalene. The temperature was increased to 100° C. and the reaction mixture was soaked at this temperature for one hour. The reaction mixture was then quenched with an ammonium hydroxide solution. The organic layer was separated, dried and stripped under vacuum at 200° C. $C^{13}$ NMR analysis showed a mixture of mono- and di-alkylated naphthalene. The reaction scheme is shown, below:

Synthesis Example B

Linking alkylated Naphthalene

Dodecyl naphthalene (29.6 g, 0.10 mol) in 200 ml of methylene chloride was charged into a 500 ml round bottom flask. The dodecyl naphthalene was derived from naphthalene and dodecene in a manner analogous to that described in Synthesis Example A. The solution was cooled to 5° C. with stirring under a blanket of dry nitrogen. Anhydrous aluminum chloride (14.7 g) was added to the solution. A solution of adipoyl chloride (15.2 g, 0.08 mol) inlSO ml methylene chloride, was added dropwise over 30 min and the mixture were stirred for 1 hr at 5° C. The mixture was then allowed to slowly warm over 2 hr to room temperature. The mixture was subsequently poured onto 200 g of ice. The organic layer was separated in a separatory funnel, washed successively with water, 5% aqueous sodium bicarbonate and stripped on a rotary evaporator to yield 22.5 g of product (62%). An infrared spectrum of the product showed a strong absorption at 1676 cm$^{-1}$, characteristic of a conjugated aromatic ketone. Gel permeation chromatography, coupled with $C^{13}$—NMR analysis indicated that product was a trimer. The reaction scheme is shown, below:

Synthesis Example C

Alkylation of Quinoline

About 1.0 mole (129 g) quinoline and 1.0 mole (252 g) of octadecene are charged into a reaction flask. About 20 g of F-20X, an acidic clay obtained from Engelhard Chemicals, are added to the reaction flask and the reaction mixture is slowly heated to 180° C. while stirring under nitrogen. The reaction mixture is then soaked at this temperature for four hours. The reaction mixture is diluted in heptane and filtered to separate the solid catalyst. The heptane solution is then stripped under nitrogen at 100° C. until constant weight. The product obtained is a mixture of mono-/di-substituted as indicated by GC analysis. If one desires the di-substituted product to be the major component, an excess olefin can be used. The reaction scheme is shown, below:

Synthesis Example D
Linking Alkylated Quinoline

About 38.1 g (0.1 mole) of octadecyl quinoline in 200 ml of methylene chloride was charged into a 500 ml round bottom flask. The solution was cooled to 5° C. with stirring under a blanket of dry nitrogen. Anhydrous aluminum chloride (14.7 g) was added to the solution. A solution of adipoyl chloride (15.2 g, 0.08 mol) in 150 ml methylene chloride, was added dropwise over 30 min and the mixture were stirred for 1 hr at 5° C. The mixture was then allowed to slowly warm over 2 hr to room temperature. The mixture was subsequently poured onto 200 g of ice. The organic layer was separated in a separatory funnel, washed successively with water and 5% aqueous sodium bicarbonate and stripped on a rotary evaporator to yield 22.5 g of product (62%). An infrared spectrum of the product showed a strong absorption at 1676 cm$^{-1}$, characteristic of a conjugated aromatic ketone. Gel permeation chromatography indicated that product contained on average three alkyl quinoline units per chain. The reaction scheme is shown, below:

Example 1

The ability of a composition to control soot-induced viscosity increase, and thus, the ability of a composition to maintain soot in suspension, can be measured using bench tests, such as a Haake Carbon Black Test. The Haake Carbon Black Test involves the blending of a base oil and additive components to provide a formulated oil. Carbon black powder is then added to the formulated oil and the sample is blended overnight. The viscosity of the carbon black dispersion is then measured in the Haake rheometer over a range of shear rates from 0.1 sec$^{-1}$ to 30 sec$^{-1}$. Typically, the viscosity at shear rates of 0.26 sec$^{-1}$ and 0.45 sec$^{-1}$ are used for comparison.

Figure 1:
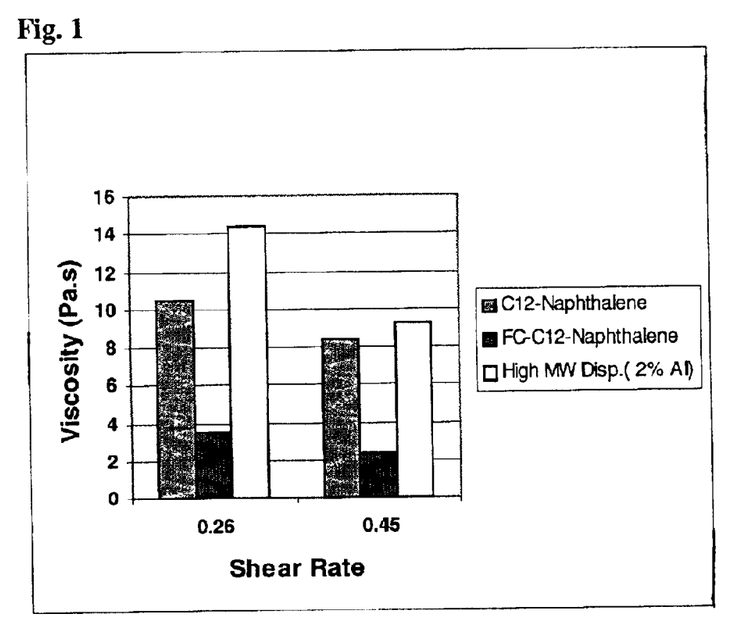
FIG. 1 compares graphically the soot induced viscosity increase, as measured using a Haake carbon black test, in a formulated lubricating oil containing a high molecular weight dispersant; a formulated lubricating oil containing a combination of a high molecular weight dispersant and 1 wt. % of an alkylated, linked aromatic oligomer of the present invention; and a formulated lubricating oil containing a combination of a high molecular weight dispersant and 1 wt. % of a comparative, unlinked alkylated aromatic compound.
Figure 2:
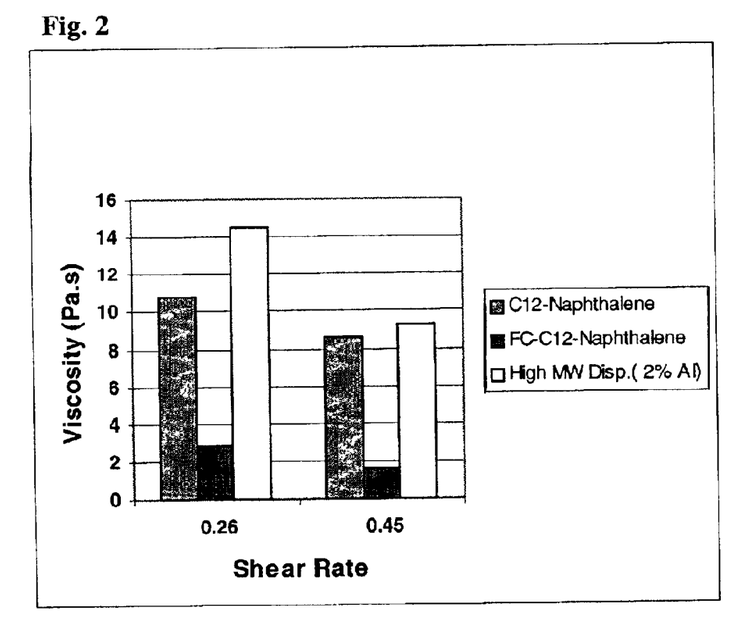
FIG. 2 compares graphically the soot induced viscosity increase, as measured using a Haake carbon black test, in a formulated lubricating oil containing a high molecular weight dispersant; a formulated lubricating oil containing a combination of a high molecular weight dispersant and 2 wt. % of an alkylated, linked aromatic oligomer of the present invention; and a formulated lubricating oil containing a combination of a high molecular weight dispersant and 2 wt. % of a comparative, unlinked alkylated aromatic compound.

The performance of the linked aromatic oligomer of the present invention as a dispersant booster was tested in the Haake rheometer using a formulated oil containing detergent, antioxidant, antiwear agent and 4 wt. % (2% AI) of a high molecular weight PIBSA-PAM dispersant. The high molecular weight PIBSA-PAM dispersant was derived from PIBSA having a molecular weight of about 2200, and a succination ratio of about 1.1. The formulated oils were tested at a 4.76% carbon black level. The results with formulated oils containing 1 wt. % and 2 wt. % of the linked aromatic oligomer additive are presented in FIGS. 1 and 2, respectively. The linked aromatic oligomer additive was the reaction product of the Friedel Craft reaction of the C$_{12}$ alkylated naphthalene with adipoyl chloride as described in Synthesis Example B. For comparison, formulations containing an analogous, unlinked alkylated naphthalene at 1 wt. % and 2 wt. %., and a formulation containing 4 wt. % (2% AI) of the high molecular weight dispersant, were also tested. The results, as shown in FIG. 1 and FIG. 2, clearly demonstrate the superior control of soot induced viscosity increase (a reduction in viscosity of at least 70%) in formulations containing 4 wt. % (2% AI) of a high molecular weight dispersant and a minor amount (1 or 2 wt. %) of the linked aromatic oligomer of the present invention, when compared to (A) formulations containing 4 wt. % (2% AI) of a high molecular weight dispersant and 1 or 2 wt. % of alkylated naphthalene and (B) formulations containing only 4 wt. % (2% AI) of a high molecular weight dispersant.

The disclosures of all patents, articles and other materials described herein are hereby incorporated, in their entirety, into this specification by reference. The principles, preferred embodiments and modes of operation of the present invention have been described in the foregoing specification. What applicants submit is their invention, however, is not to be construed as limited to the particular embodiments disclosed, since the disclosed embodiments are regarded as illustrative rather than limiting. Changes may be made by those skilled in the art without departing from the spirit of the invention.

What is claimed is:

1. A lubricating oil composition comprising a major amount of an oil of lubricating viscosity; a minor amount of a high molecular weight, nitrogen-containing dispersant; and a minor amount of an oligomer of the formula:

(I)

wherein each Ar independently represents an aromatic moiety selected from polynuclear carbocyclic moieties, said aromatic moiety being optionally substituted by 1 to 6 substituents selected from H, —$OR_1$, —$N(R_1)_2$, F, Cl, Br, I, -(L-(Ar)-T), —$S(O)_wR_1$, -$(CZ)_y$-$(Z)_y$—R, and -$(Z)_y$-$(CZ)_x$—$R_1$, wherein w is 0 to 3, each Z is independently O, —$N(R_1)_2$ or S, x and y are independently 0 or 1 and each $R_1$ is independently H or a linear or branched, saturated or unsaturated hydrocarbyl group having from 1 to about 200 carbon atoms, optionally mono- or poly-substituted with one or more groups selected from —$OR_2$, —$N(R_2)_2$, F, Cl, Br, I, —$S(O)_wR_2$, -$(CZ)_x$-$(Z)_y$—$R_2$ and -$(Z)_y$-$(CZ)_x$—$R_2$, wherein w, x, y and Z are as defined above and $R_2$ is a hydrocarbyl group having 1 to about 200 carbon atoms;

each L is independently a linking moiety comprising a carbon—carbon single bond or a linking group;

each T is independently H, $OR_1$, $N(R_1)_2$, F, Cl, Br, I, $S(O)_wR_1$, $(CZ)_x$-$(Z)_y$—$R_1$ or $(Z)_y$-$(CZ)_x$—$R_1$, wherein $R_1$, w, x, y and Z are as defined above; and n is 2 to about 1000;

wherein at least 25% of aromatic moieties (Ar) are connected to at least 2 linking moieties (L) and a ratio of the total number of aliphatic carbon atoms in the oligomer to the total number of aromatic ring atoms in aromatic moieties (Ar) is from about 0.10:1 to about 40:1.

2. The lubricating oil composition of claim 1, wherein said ratio of the total number of aliphatic carbon atoms in the oligomer to the total number of aromatic ring atoms in aromatic moieties (Ar) is from about 4:1 to about 7:1.

3. The lubricating oil composition of claim 1, wherein at least 60% of aromatic moieties (Ar) are substituted.

4. The lubricating oil composition of claim 1, wherein hydrocarbyl groups $R_1$ and $R_2$ have from 1 to about 30 carbon atoms.

5. The lubricating oil composition of claim 1, wherein each of said linking moieties (L) is independently selected from an alkylene linkage, an ether linkage, an ester linkage, an anhydride linkage, an ether-acyl linkage, an ether ester linkage, an acyl-ester linkage, an amino linkage, an amido linkage, a carbamido linkage, a urethane linkage and a sulfur linkage, each of the linkage groups being optionally mono- or polysubstituted with $OR_1$, $N(R_1)_2$, F, Cl, Br, I, $S(O)_wR_1$, $(CZ)_x$-$(Z)_y$—$R_1$ or $(Z)_y$-$(CZ)_x$—$R_1$, wherein w, Z and $R_1$ are as defined in claim 1.

6. The lubricating oil composition of claim 5, wherein said linkage moieties are selected from alkylene linkages —$CH_3CHC(CH_3)_2$- and —$C(CH_3)_2$-, diacyl linkages— COCO— and —$CO(CH_2)_4CO$—, and sulfur linkages —$S_1$- and —$S_2$—.

7. The lubricating oil composition of claim 1, wherein aromatic moiety (Ar) is selected from naphthalene and quinoline.

8. The lubricating oil composition of claim 1, wherein said high molecular weight dispersant is present in an amount providing from about 0.008 to about 0.32 wt. % of nitrogen, and said oligomer is present in an amount of from about 0.005 to about 10 wt. %, based on the total weight of lubricating oil composition.

9. An oligomer of the formula:

(I)

wherein each Ar independently represents an aromatic moiety selected from polynuclear carbocyclic moieties, said aromatic moiety being optionally substituted by 1 to 6 substituents selected from H, —$OR_4$, —$N(R_4)_2$, F, Cl, Br, I, —(L-(Ar)-T), —$S(O)_wR_4$, -$(CZ)_x$-$(Z)_y$—$R_4$ and -$(Z)_y$-$(CZ)_x$—$R_4$, wherein w is 0 to 3, each Z is independently O, —$N(R_4)_2$ or S, x and y are independently 0 or 1 and each $R_4$ is independently H, methyl, ethyl, propyl or a branched hydrocarbyl group having 3 to 200 carbon atoms, optionally mono- or poly-substituted with one or more groups selected from —$OR_4$, —$N(R_4)_2$, F, Cl, Br, I, —$S(O)_wR_4$, —$(CZ)_x$—$(Z)_y$—$R_4$ and -$(Z)_y$-$(CZ)_xR_4$, wherein w, x, y R4 and Z are as defined above;

each L is independently a linking moiety comprising a carbon—carbon single bond or a linking group;

each T is independently H, $OR_1$, $N(R_4)_2$, F, Cl, Br, I, $S(O)_wR_4$, $(CZ)_x$—$(Z)_y$—$R_4$ or $(Z)_y$-$(CZ)_x$—$R_4$, wherein $R_4$, w, x, y and Z are as defined above; and n is 2 to about 1000;

wherein at least 25% of aromatic moieties (Ar) are connected to at least 2 linking moieties (L) and a ratio of the total number of aliphatic carbon atoms in the oligomer to the total number of aromatic ring atoms in aromatic moieties (Ar) is from about 0.10:1 to about 40:1.

10. The oligomer of claim 9, wherein said ratio of the total number of aliphatic carbon atoms in the oligomer to the total number of aromatic ring atoms in aromatic moieties (Ar) is from about 4:1 to about 7:1.

11. The oligomer of claim 9, wherein at least 60% of aromatic moieties (Ar) are substituted.

12. The oligomer of claim 9, wherein hydrocarbyl groups $R_4$ and $R_5$ have from 1 to about 30 carbon atoms.

13. The oligomer of claim 9, wherein each of said linking moieties (L) is independently selected from an alkylene linkage, an ether linkage, an ester linkage, an anhydride linkage, an ether-acyl linkage, an ether ester linkage, an acyl-ester linkage, an amino linkage, an amido linkage, a carbamido linkage, a urethane linkage and a sulfur linkage, each of the linkage groups being optionally mono- or polysubstituted with $OR_1$, $N(R_1)_2$, F, Cl, Br, I, $S(O)_wR_I$, $(CZ)_x$-$(Z)_y$—$R_1$ or $(Z)_y$-$(CZ)_x$—$R_1$, wherein w, Z and $R_1$ are as defined in claim 1.

14. The oligomer of claim 13, wherein said linkage moieties are selected from alkylene linkages —$CH_3CHC(CH_3)_2$— and —$C(CH_3)_2$—, diacyl linkages—COCO— and —$CO(CH_2)_4CO$—, and sulfur linkages —$S_1$-and —$S_2$—.

15. The oligomer of claim 9, wherein aromatic moiety (Ar) is selected from naphthalene and quinoline.

* * * * *

UNITED STATES PATENT AND TRADEMARK OFFICE
CERTIFICATE OF CORRECTION

| | | |
|---|---|---|
| PATENT NO. | : 6,750,183 B2 | Page 1 of 1 |
| APPLICATION NO. | : 09/746044 | |
| DATED | : June 15, 2004 | |
| INVENTOR(S) | : Gutierrez et al. | |

It is certified that error appears in the above-identified patent and that said Letters Patent is hereby corrected as shown below:

In claim 1, line 9, change "—$(CZ)_y$—$(Z)_y$—R" to -- —$(CZ)_x$—$(Z)_y$—$R_1$-- and in line 63, change "allenyl" to --alkenyl--.

In claim 9, line 17, change "200" to --36--

In claim 9, line 19, change "—$OR_4$, —$N(R_4)_2$, F, Cl, Br, I, —$S(O)_wR_4$," to -- —$OR_5$, —$N(R_5)_2$, F, Cl, Br, I, —$S(O)_wR_5$,--

In claim 9, line 20, change "$(Z)_y$—$R_4$" to --$(Z)_y$—$R_5$-- and change "$(CZ)_xR_4$" to --$(CZ)_xR_5$--.

In claim 9, line 20, after "w, x, y" delete --R4--.

In claim 9, line 21, after "above" add --and $R_5$ is a hydrocarbyl group having 1 to about 200 carbon atoms--.

Signed and Sealed this

Twenty-fourth Day of April, 2007

JON W. DUDAS
*Director of the United States Patent and Trademark Office*